United States Patent [19]

Leighton

[11] 4,103,689

[45] Aug. 1, 1978

[54] TISSUE PRESSURE REFERENCE FOR CEREBROSPINAL FLUID SHUNTING DEVICE

[76] Inventor: Stephen Beecher Leighton, 93 Jefferson Ave., Maplewood, N.J. 07040

[21] Appl. No.: 750,154

[22] Filed: Dec. 13, 1976

[51] Int. Cl.² ........................................... A61M 27/00
[52] U.S. Cl. ................................. 128/350 V; 128/274
[58] Field of Search ............. 128/350 R, 350 V, 274; 251/4–10

[56] References Cited

U.S. PATENT DOCUMENTS

| 3,396,448 | 8/1968 | Kisling | 251/5 |
| 3,463,159 | 8/1969 | Heimlich | 128/350 V |
| 3,624,800 | 11/1971 | Swick | 251/4 |
| 3,733,046 | 5/1973 | Press | 251/4 |
| 3,769,982 | 11/1973 | Schulte | 128/350 V |
| 3,991,768 | 11/1976 | Portnoy | 128/350 V |

FOREIGN PATENT DOCUMENTS 1,211,941  10/1959  France ................................. 128/350 R Primary Examiner—Dalton L. Truluck

[57] ABSTRACT

A device to be used as part of an artificial shunt for abnormal intracranial pressure conditions. A compliant tube of unique cross-section acts as a pressure regulator, preventing siphoning of cerebrospinal fluid under conditions of reduced pressure at the distal end of the shunt.

5 Claims, 5 Drawing Figures

TISSUE PRESSURE REFERENCE FOR CEREBROSPINAL FLUID SHUNTING DEVICE

FIELD OF THE INVENTION

The present invention relates to artificial implantable pressure regulators for surgical use, and, more particularly, to those devices which use internal tissue pressure, or atmospheric pressure, as a reference.

BACKGROUND OF THE INVENTION

Conditions of abnormally increased intracranial pressure are often treated surgically by the implantation of an artificial tube, or shunt, to conduct excess fluid from the intracranial space to another part of the body, for example, to the peritoneum or right atrium of the heart. These shunt tubes are typically non-collapsible. A differential pressure valve is often inserted in series with the tube, to maintain upstream pressure at least a certain amount above downstream pressure.

However, in the upright posture, the downstream pressure can drop low enough that the upstream, intracranial pressure, drops to abnormally low values, despite the differential pressure valve.

Attempts to solve this problem have fallen into two classes. Differential diaphragm valves allegedly reference atmospheric pressure to prevent siphoning. These, however, have a complicated structure, subject to clogging with tissue debris, and their exterior design, of limited area, is subject to interference by scar tissue. Gravity sensitive valves, the second class, attempt to sense the angular position of the body with a weight or other device, but they are only sensitive to body position at one location, and are often non-linear.

SUMMARY

An objective of this invention, therefore, is to provide an improved method and device for controlling the pressure in patients with artificial shunts for cerebrospinal fluid.

Another objective of the invention is to provide a device which is simple to construct and to implant.

Another objective of the invention is to provide a device which is not likely to become clogged or to provide a stagnant site for growth of bacteria.

Another objective of the invention is to provide a system which controls intracranial pressure with respect to tissue pressure at a desireable location, such as the neck.

Other objectives and advantages will become apparent from the following more complete description, it being understood that the specific embodiment set forth is exemplary.

Broadly, the invention contemplates a method and device for controlling intracranial pressure which is shunted by an artificial shunt. The method and device includes a collapsible tube having a cross-section such that under a condition of zero transmural pressure (that is, outside pressure equal to inside pressure) the tube is substantially closed.

DETAILED DESCRIPTION OF EMBODIMENT

Figure 1:
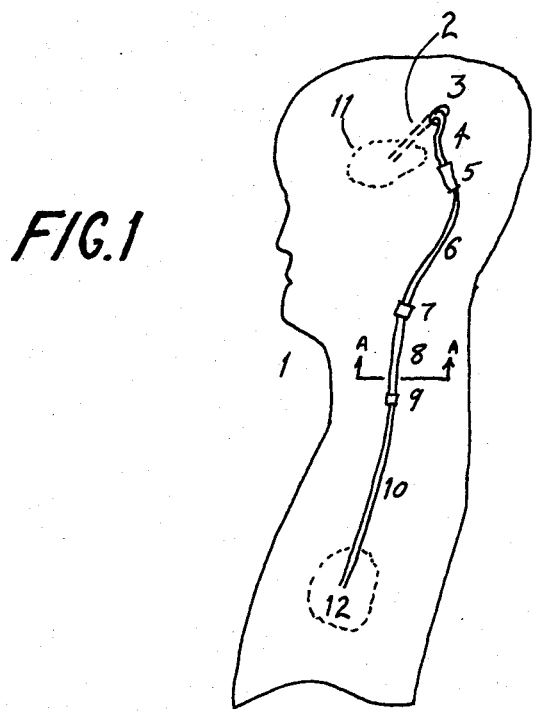
FIG. 1 Shows a substantially complete shunt system implanted in a patient with skin removed to show the shunt.

Referring now to the figures wherein like reference numerals designate like parts throughout the several views thereof, there is shown in FIG. 1 a patient 1 in whom a substantially complete shunt system has been implanted. In the head of 1, there is placed a tube 2 through a hole 3 in the skull, for example. The tube 2 connects with a tube 4 and thence with a differential pressure valve 5. Cerebrospinal fluid can flow from within a cranial cavity 11, through tubes 2 and 4, valve 5, tube 6 connector 7, tube 8, connector 9, and tube 10 to a drainage site 12. Tubes 2, 4, 6 and 10 are typically, but not necessarily, of round, thick wall, non-collapsing cross-section.

Figure 2:
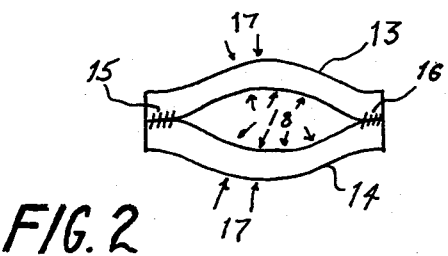
FIG. 2 Shows a cross-sectional view of the tube of the invention as it would appear at section AA of FIG. 1 with an internal pressure moderately greater than the external pressure.
Figure 3:
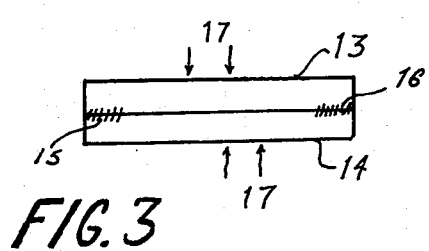
FIG. 3 Shows a cross-sectional view of the tube as it would appear with an internal pressure equal to or less than the external pressure.

Tube 8 is shown in detail cross-section in FIG. 2. The pressure regulator tube consists of sidewalls 13 and 14 which may be bonded together as shown at 15 and 16 or formed as one piece or made by a number of other methods. When this tube 8 is relaxed, that is, when the external pressure 17 and internal pressure 18 are equal, it will have the form shown in FIG. 3.

Thus, there will be a significant pressure drop in the tube 8 even with extremely low flowrates, if the inside pressure is less than the outside pressure. Thus, if pressure near the distal end 9 of tube 8 is reduced below the pressure on the outside of tube 8, then tube 8 will tend to close, preventing the pressure in the proximal end 7 from falling below the pressure just outside tube 8. The lengths and sequence of the various tubes may be varied. The cross-sectional dimensions, lengths, and materials of the collapsible section may be chosen to give a desired pressure vs. flow characteristic.

Figure 4:
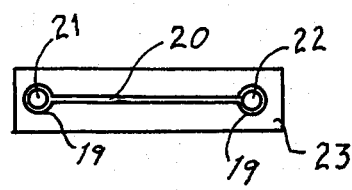
FIG. 4 and FIG. 5 show examples of functionally similar cross-sections.

FIG. 4 shows an alternate cross-section which will function similarly. The ends 19 of the lumen, 20, are rounded to reduce stress concentrations, and filled with material 21 and 22 to give a substantially closed cross-section when transmural pressure is low. The wall of the tube, 23, is, for example, formed as one piece.

Figure 5:
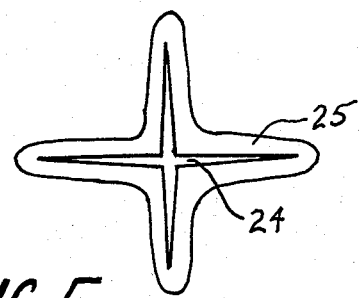

FIG. 5 shows an alternate cross-section. The lumen 24 is shown slightly expanded for clarity. The wall, 25, is, for example, made of one piece.

From the above description of the structure and operation of the invention, it is clear that there is disclosed an improved method and device for controlling intracranial pressure.

Obviously many modifications and variations of the present invention are possible in the light of the above teachings. It is therefore understood, that within the scope of the appended claims, the invention may be practiced otherwise than as specifically described; and that modifications and adaptations may be made without departing from the invention.

What is claimed is:

1. A hydrocephalus shunt system comprising an inlet tube for connection to the ventricles of the brain, and an outlet tube for connection to a body cavity downstream, and interposed there between a pressure regulating collapsible tube, the improvement wherein said collapsible tube consists of an annular walled structure of compliant material having closely juxtaposed sides such that in the relaxed position of zero transmural pressure, the lumen of the tube has a substantially closed cross-section and wherein the collapsible section is substantially free of a case or compartment or enclosure or inner wall spacing means of any kind and wherein intimate contact of the collapsible section with body tissue is maintained said collapsible tube being connected to and supported at its ends by said inlet and outlet tubes.

2. The device of claim 1 combined with a differential pressure valve.

3. The device of claim 1 wherein the collapsible section comprises two flat strips bonded together along their edges parallel to the axis of flow.

4. The device of claiim 1 wherein the collapsible section comprises a slit for a fluid passage, said slit having rounded edges to prevent stress concentrations, said rounded edges being filled to prevent fluid flow in the relaxed state.

5. The device of claim 1 wherein the collapsible section comprises a cruciate cross-section.

* * * * *